United States Patent [19]
Meng et al.

[11] Patent Number: 5,608,036
[45] Date of Patent: Mar. 4, 1997

[54] ENHANCED SECRETION OF POLYPEPTIDES

[75] Inventors: Shi-Yuan Meng, Agoura Hills; Charles F. Morris, Newbury Park; Larry B. Tsai, Agoura, all of Calif.

[73] Assignee: Amgen Inc., Thousand Oaks, Calif.

[21] Appl. No.: 407,344

[22] Filed: Mar. 20, 1995

Related U.S. Application Data

[62] Division of Ser. No. 215,138, Mar. 18, 1994, Pat. No. 5,470,719.

[51] Int. Cl.$^6$ .................. C07K 14/00; C07K 14/475; C07K 14/48
[52] U.S. Cl. .................. 530/324; 435/69.8; 530/326; 514/13
[58] Field of Search .................. 530/326, 324; 514/13; 435/69.8

[56] References Cited

U.S. PATENT DOCUMENTS

| | | | |
|---|---|---|---|
| 4,338,397 | 7/1982 | Gilbert et al. | 435/69.1 |
| 4,757,013 | 7/1988 | Inouye et al. | 435/172.3 |
| 5,235,043 | 8/1993 | Collins et al. | 530/399 |
| 5,474,914 | 12/1995 | Spaete | 435/69.1 |

FOREIGN PATENT DOCUMENTS

| | | |
|---|---|---|
| WO92/05254 | 4/1992 | WIPO . |
| WO93/25684 | 12/1993 | WIPO . |

OTHER PUBLICATIONS

Gennity et al., Signal Peptide Mutants of *Escherichia coli*, *Journal of Bioenergetics and Biomembranes*, pp. 233–269, vol. 22, No. 3, 1990.

Goldstein et al., Enhancement of Protein Translocation across the Membrane by Specific Mutations in the Hydrophobic Region of the Signal Peptide, *Journal of Bacteriology*, pp. 1225–1231, vol. 172, No. 3, 1989.

Hallböök et al., Evolutionary Studies of the Nerve Growth Factor Family Reveal a Novel Member Abundantly Expressed in Xenopus Ovary, *Neuron*, pp. 845–848, vol. 6, May, 1991.

Lehnhardt et al., Modulation of the Effects of Mutations in the Basic Region of the OmpA Signal Peptide by the Mature Portion of the Protein, *Journal of Biological Chemistry*, pp. 10300–10303, vol. 263, No. 21, Jul. 1988.

Lehnhardt et al., The Differential Effect on Two Hybrid Proteins of Deletion Mutations within the Hydrophobic Region of the *Escheria coli* OmpA Signal Peptide, *Journal of Biological Chemistry*, pp. 1716–1719, vol. 262, No. 4, Feb. 1987.

Kaisho et al., Cloning and expression of a cDNA encoding a novel human neurotrophic factor, *Febs Letters*, pp. 187–191, vol. 266, No. 1, 2, Jun. 1990.

Maisonpierre et al., Human and Rat Brain–Derived Neurotrophic Factor and Neurotrophin–3: Gene Structures, Distributions, and Chromosomal Localizations, *Genomics* 10, pp. 558–568, 1991.

Narhi et al., Comparison of the Biophysical Characteristics of Human Brain–derived Neurotrophic Factor, Neurotrophin–3, and Nerve Growth Factor, *Journal of Biological Chemistry*, pp. 13309–13317, vol. 268, No. 18, Jun. 1993.

Rosenthal et al., Primary Structure and Biological Activity of a Novel Human Neurotrophic Factor, *Neuron*, pp. 767–773, vol. 4, May 1990.

Tanji et al., Effect of OmpA Signal Peptide Mutations on OmpA Secretion, Synthesis, and Assembly, *Journal of Bacteriology*, pp. 1997–2005, vol. 173, No. 6, Mar. 1991.

*Primary Examiner*—Stephen G. Walsh
*Assistant Examiner*—Stephen Gucker
*Attorney, Agent, or Firm*—Nancy A. Oleski

[57] ABSTRACT

A signal peptide sequence and nucleic acids encoding this sequence which are useful for improving the secretion efficiency of NGF polypeptides are provided. Also provided is a method for preparing Met-less NGF polypeptides.

4 Claims, 8 Drawing Sheets

FIG. 1

MKKRARAIAI AVALAGFATV AHA

FIG. 2

ATGAARAARC GYGCDCGYGC DATYGCDATY GCDGTWGCDC TGGCDGGYTT

YGCDACYGTW GCDCAYGCD

FIG. 3

ATGAAAAAGC GCGCGCGTGC GATCGCGATC GCGGTTGCGC TGGCTGGCTT

CGCTACCGTT GCGCACGCT

FIG. 4A

ATGCACTCTG ACCCGGCTCG TCGTGGTGAA CTGTCTGTTT GTGATTCTAT

CTCTGAATGG GTTACCGCGG CTGATAAGAA AACCGCAGTC GACATGTCTG

GTGGCACTGT TACCGTCCTC GAGAAAGTTC CTGTATCTAA AGGTCAGCTG

AAACAATATT TCTACGAAAC CAAATGCAAT CCGATGGGTT ACACTAAAGA

AGGCTGCCGT GGCATCGACA AACGTCATTG GAACTCTCAG TGTCGTACTA

CCCAGTCTTA TGTTCGTGCG CTGACCATGG ACTCCAAGAA ACGTATCGGC

TGGCGCTTCA TCCGTATTGA CACTAGTTGC GTTTGTACTC TGACTATCAA

ACGTGGCCGC TAA

FIG. 4B

CACTCTGACC CGGCTCGTCG TGGTGAACTG TCTGTTTGTG ATTCTATCTC

TGAATGGGTT ACCGCGGCTG ATAAGAAAAC CGCAGTCGAC ATGTCTGGTG

GCACTGTTAC CGTCCTCGAG AAAGTTCCTG TATCTAAAGG TCAGCTGAAA

CAATATTTCT ACGAAACCAA ATGCAATCCG ATGGGTTACA CTAAAGAAGG

CTGCCGTGGC ATCGACAAAC GTCATTGGAA CTCTCAGTGT CGTACTACCC

AGTCTTATGT TCGTGCGCTG ACCATGGACT CCAAGAAACG TATCGGCTGG

CGCTTCATCC GTATTGACAC TAGTTGCGTT TGTACTCTGA CTATCAAACG

TGGCCGCTAA

FIG. 5A

ATGTACGCTG AACACAAATC CCACCGTGGT GAATATTCCG TTTGCGACTC

CGAATCCCTG TGGGTTACCG ACAAATCCTC CGCTATCGAT ATCCGTGGTC

ACCAGGTTAC CGTTCTGGGT GAAATCAAAA CCGGTAACTC CCCAGTAAAA

CAGTACTTCT ACGAAACCCG TTGCAAAGAA GCTCGTCCGG TTAAAAACGG

TTGCCGCGGT ATCGACGACA AACATTGGAA CTCTCAGTGC AAAACTAGTC

AGACCTACGT TCGTGCTCTG ACCTCCGAAA ACAACAAGCT TGTTGGTTGG

CGTTGGATTC GTATCGACAC CAGCTGCGTT TGCGCTCTGT CCCGTAAAAT

CGGTCGTACC TAA

FIG. 5B

TACGCTGAAC ACAAATCCCA CCGTGGTGAA TATTCCGTTT GCGACTCCGA

ATCCCTGTGG GTTACCGACA AATCCTCCGC TATCGATATC CGTGGTCACC

AGGTTACCGT TCTGGGTGAA ATCAAAACCG GTAACTCCCC AGTAAAACAG

TACTTCTACG AAACCCGTTG CAAAGAAGCT CGTCCGGTTA AAACGGTTG

CCGCGGTATC GACGACAAAC ATTGGAACTC TCAGTGCAAA ACTAGTCAGA

CCTACGTTCG TGCTCTGACC TCCGAAAACA ACAAGCTTGT TGGTTGGCGT

TGGATTCGTA TCGACACCAG CTGCGTTTGC GCTCTGTCCC GTAAAATCGG

TCGTACCTAA

ENHANCED SECRETION OF POLYPEPTIDES

This application is a division, of application Ser. No. 08/215,138, filed Mar. 18, 1994, U.S. Pat. No. 5,470,719, which is hereby incorporated by reference.

FIELD OF THE INVENTION

This invention relates to novel signal peptide and nucleic acid sequences useful for enhancing secretion of certain polypeptides. The invention further relates to a method for increasing the efficiency of secretion of these polypeptides from bacterial cells.

BACKGROUND

Direct Expression of Polypeptides

Many polypeptides of pharmaceutical importance are prepared in prokaryotic cells such as bacteria using recombinant DNA techniques. The DNA encoding the polypeptide (often obtained from human tissues) can be inserted into the "host" cell where it is expressed, (i.e. translated) from DNA to polypeptide in the cytoplasm. The polypeptide is then purified from the host cells. This procedure is often referred to as "direct" expression of a polypeptide.

While direct expression of a polypeptide is often the most convenient way to manufacture the polypeptide, there can be problems associated with this method.

For example, as the polypeptide is synthesized in the host cell and begins to accumulate, the polypeptide may become toxic to the host cell and kill it. In addition, intracellular proteases may rapidly degrade the polypeptide molecules as they are synthesized. Further, as the intracellular concentration of the polypeptide increases, the host cell machinery may cease manufacturing via a "feedback mechanism" in the host cell directing termination of polypeptide synthesis. One other possibility is that polypeptides that remain in the cytoplasm after synthesis may be subjected to post-translational modification such as acetylation.

Secretion of Polypeptides

To circumvent problems associated with direct expression of polypeptides, other methods for expression of the polypeptide have been developed. One such method, termed "indirect expression", permits the polypeptide to be secreted from the host cell as it is produced. This method is also referred to as "secretion" or "processing" of the polypeptide. After secretion, the polypeptide can be isolated from the culture medium, or, in the case of gram-negative bacterial host cells, from the periplasmic space or "periplasm", the area between the inner and outer cellular membranes. The use of secretion therefore may help to decrease the problems associated with intracellular accumulation of the polypeptide.

Some polypeptides naturally produced by bacterial cells (and other cells) are secreted from these cells into the extracellular environment (or, in the case of gram negative bacteria, into the periplasm). Secretion of a polypeptide from a bacterial cell appears to involve the orchestration of several intracellular proteins known as chaperone proteins (Zhu et al., *Pharm. Tech.*, April 1993, pp. 28–38; Simonen et al., *Microbiol. Rev.*, 57:109–137 [1993]) that identify the polypeptide to be secreted, and aid it in the secretory process.

Secreted polypeptides typically have the following structure: they contain as part of the amino acid sequence a signal peptide (also known as a leader peptide, leader sequence, or signal sequence). A signal peptide is typically a relatively small peptide, and is usually synthesized as the amino terminal portion of the polypeptide during translation. The polypeptide with its signal peptide attached is often referred to as the "precursor polypeptide" or the "immature form of the polypeptide". The signal peptide directs the full-length polypeptide across the cell membrane. In the course of secretion of the polypeptide, the signal peptide is cleaved. As a result, only the "mature" form of the polypeptide is secreted across the cell membrane (or the inner cell membrane for gram-negative bacteria, as discussed below). Since the signal peptide is cleaved, the mature polypeptide typically has a smaller molecular weight as compared to the precursor polypeptides.

The nucleic acid sequences, or genes, encoding most naturally occurring polypeptides that are destined for secretion typically comprise the DNA sequence for the precursor polypeptide, i.e., the 5' end of the gene contains the sequence encoding the signal peptide, and the 3' end of the signal sequence DNA is attached to the 5' end of the sequence encoding the mature form of the polypeptide. Therefore, during translation, the precursor polypeptide is synthesized as a single unit with the signal sequence at the amino terminus of the polypeptide. Many prokaryotic signal peptides have now been identified (See for example, Gennity et al., *J. Bioenerg. Biomemb.*, 22:233–269 [1990]).

Signal peptides often share certain structural features. For example, many signal peptides of prokaryotic origin are about 20–30 amino acids in length. Further, the amino terminus of the signal peptide is typically positively charged and the central portion of the signal peptide is typically hydrophobic (Pugsley (*Microbiol. Rev.*, 57:50–108 [1993]). In spite of these similarities, each secreted polypeptide currently identified in some prokaryotic organisms, such as the bacterium *E. coli*, possesses a unique signal peptide sequence. In addition, not all types of cells "recognize" and therefore have the ability to process all signal peptide sequences. A particular signal peptide may be recognized and thus capable of directing a polypeptide across the cell membrane in certain prokaryotic cells, but not be functional in eukaryotic cells.

A polypeptide not normally secreted by a prokaryotic cell can be engineered for secretion using recombinant DNA technology. This may be accomplished by creating a nucleic acid construct wherein the DNA encoding the polypeptide is attached at its 5' end to a naturally occurring or synthetic DNA sequence encoding a signal peptide. For secretion, the signal peptide sequence selected must be one that is recognized by, and is therefore capable of being processed by, the host cell into which this construct is to be inserted and expressed. Thus, for example, a signal peptide obtained from a naturally secreted bacterial polypeptide can be attached to a polypeptide from a source such as human tissue thereby creating a hybrid precursor polypeptide that can be synthesized in, and secreted from, those bacterial (and other prokaryotic) cell species that recognize and are able to process the signal peptide. The hybrid construct can be introduced into the host cell, and the host cell then may have the capability of manufacturing and secreting the polypeptide.

A number of factors determine the actual amount of polypeptide that is produced by a bacterial cell (aside from whether or not the polypeptide is secreted from the cell). Such factors as culturing conditions (Jacques et al., *J. Mol.*

Biol., 226:597–608 [1992]), the rate of translation initiation (Gold, *Ann. Rev. Biochem.*, 57:199–233 [1988]), and the rate of polypeptide degradation in the cell (due at least in part to intracellular proteases) also appear to affect the rate and amount of polypeptide that is secreted. In addition, it has been found that the type of amino acid residues present at the amino terminus of the mature polypeptide appear to have an effect on secretion; secretion seems to be reduced where some of these residues are positively charged (Andersson et al., *Proc. Natl. Acad. Sci. USA*, 88:9751–9754 [1991]).

"Met-less" Polypeptides

Many therapeutically useful human polypeptides are manufactured in prokaryotic cells such as bacteria using recombinant DNA methods.

A heterologous polypeptide (such as a human polypeptide) manufactured in prokaryotic cells using recombinant DNA technology is not always identical to the naturally occurring form of the polypeptide. The two forms may differ slightly in their chemical structure. For example, many human polypeptides manufactured in bacterial host cells using recombinant DNA technology have the amino acid methionine, "Met", at the amino terminus ("amino-terminal Met"). These same human polypeptides in their naturally occurring form often do not contain the amino terminal Met, as it is usually removed during secretion of the polypeptides from the human cell where they are naturally synthesized into the bloodstream or other extracellular fluid where they are naturally found.

In some cases where human polypeptides are synthesized in prokaryotic cells, the amino terminal methionine may be removed by a host cell cytoplasmic methionine aminopeptidase, however this removal, or cleavage is seldom complete where the polypeptide is over-expressed in the host cell.

NGF Polypeptides

The NGF(nerve growth factor) family of polypeptides, or "NGF polypeptides" are a group of structurally and functionally related neurotrophic factors that are found in many cells and tissues of the nervous system and in tissues that are innervated with components of the nervous system. At present, the NGF polypeptide family comprises the polypeptides BDNF (brain derived neurotrophic factor), NGF (nerve growth factor) NT-3 (neurotrophin-3), NT-4 (neurotrophin-4; described in PCT 93/25684 published 23 Dec. 1993; PCT 92/05254 published 2 April 1992; Hallbook et al., *Neuron*, 6:845–858 [1991]), and NT-5. These polypeptides have been demonstrated to function in the growth, survival, and/or differentiation of various types of nerve cells.

BDNF, NT-3, NGF, and NT-4 share significant amino acid sequence homology. BDNF and NGF are about 55% homologous at the amino acid level, and NT-3 is about 58% homologous to BDNF and about 57% homologous to NGF (Narhi et al., *J. Biol. Chem.*, 268:13309–17 [1993]). NT-4 is approximately 46%, 55%, and 52% homologous with mature NGF, BDNF, and NT-3, respectively at the amino acid sequence level (PCT 92/05254, published 2 Apr. 1992; see also Hallbook et al., Neuron, 6:845–858 [1991]). The NGF polypeptides contain several cysteine residues, and the amino acid sequence in the region of these cysteines is relatively conserved (Narhi et al., supra).

Due to their respective roles in maintenance of the nervous system, it is anticipated that NGF, NT-3, NT-4, and BDNF, when prepared in the biologically active form, will be useful as therapeutics in the treatment of various nervous system diseases and disorders. Such disorders as damage to the nervous system (via trauma, surgery, infection, exposure to toxins, and/or malnutrition), various neuropathies, Alzheimer's disease, Parkinson's disease, multiple sclerosis, amylotrophic lateral sclerosis, Huntington's chorea, extra-familial tremor, and the like.

Related Art

U.S. Pat. No. 5,235,043 issued Aug. 10, 1993 purportedly describes processes for producing mature human members of the NGF (NT-3)/BDNF family of neurotrophic proteins that are fully biologically active. The polypeptides purportedly can be secreted from host cells using a signal peptide such as the OmpA signal peptide.

U.S. Pat. No. 4,757,013 issued 12 Jul. 1988 describes a cloning plasmid useful for secretion of polypeptides in bacterial hosts. In addition to other nucleic acid sequences, the plasmid optionally contains a DNA fragment coding for the signal peptide of the OmpA protein of *E. coli*. The plasmid reportedly provides for efficient secretion across the cytoplasmic membrane.

U.S. Pat. No. 4,338,397 issued 6 Jul. 1982 describes a method for secretion of a polypeptide produced in a bacterial host cell. The method reportedly permits production of proteins free of chemical substituents such as "f-met".

Tanji et al. (*J. Bacteriol.*, 173:1997–2005 [1991]) describe certain amino acid substitutions or deletions in the OmpA signal peptide amino acid sequence.

Goldstein et al. (*J. Bacteriol.*, 172:1225–1231 [1990]) describe OmpA signal peptide mutants with altered levels of hydrophobicity. The mutants reportedly had differential abilities to act as signal peptides for two proteins across the *E. coli* cell membrane.

Lenhardt et al. (*J. Biol. Chem.*, 263:10300–03 [1988]) describe OmpA signal peptide mutants in which the net charge of the amino-terminal end was reportedly altered.

Lenhardt et al. (*J. Biol. Chem.*, 262:1716–19 [1987]) describe production of mutants of the OmpA signal peptide. The mutants had a shortened hydrophobic region, and their ability to act as secretion sequences for certain proteins was reportedly altered.

In view of the problems that have been encountered in preparing large quantities of polypeptides using recombinant DNA technology, there is a need in the art to provide methods for increasing the yield of such polypeptides produced by recombinant DNA technology. Further, there is a need in the art to provide recombinant polypeptides in the "Met-less" form.

Accordingly, it is an object of the present invention to provide a signal peptide, and nucleic acid sequences encoding the signal peptide, that serve to enhance the efficiency of secretion of a NGF polypeptide produced in a prokaryotic host cell.

It is yet a further object to provide a method for preparing NGF polypeptides in the Met-less form.

Other objects will be apparent to one of ordinary skill in the art.

SUMMARY OF THE INVENTION

Accordingly, in one aspect, the invention provides a signal peptide comprising the sequence MKKRARAIAIA-VALAGFATVAHA (SEQ ID NO:1).

In another aspect, the signal peptide may further comprise at its carboxyl terminal the polypeptide BDNF, NGF, NT-3, NT-4, or NT-5.

In another aspect, the invention provides a nucleic acid comprising a sequence as set forth in SEQ ID NO:2.

In another aspect, the invention provides a nucleic acid as set forth in SEQ ID NO:3.

In still one other aspect, the invention provides a nucleic acid as set forth in SEQ ID NO:2 or SEQ ID NO:3 that further comprises at its 3' end a nucleic acid encoding an amino-terminal Met-less NGF polypeptide.

In yet another aspect, the invention provides a vector comprising the nucleic acid as set forth in SEQ ID NO:2 or SEQ ID NO:3 linked at its 3' end to a nucleic acid encoding an amino-terminal Met-less NGF polypeptide. Optionally, the vector may be pCFM1656/BDNFopt3 or pCFM1656/NT-3opt3.

In one other aspect, the invention provides a prokaryotic host cell into which the vector has been inserted.

In one other aspect, the invention provides a method of producing a Met-less form of a NGF polypeptide comprising culturing a prokaryotic host cell into which a vector comprising the nucleic acid as set forth in SEQ ID NO:2 or SEQ ID NO:3 linked at its 3' end to a nucleic acid encoding an amino-terminal Met-less NGF polypeptide has been inserted, and isolating the secreted NGF polypeptide.

BRIEF DESCRIPTION OF THE DRAWINGS

Figure 1:
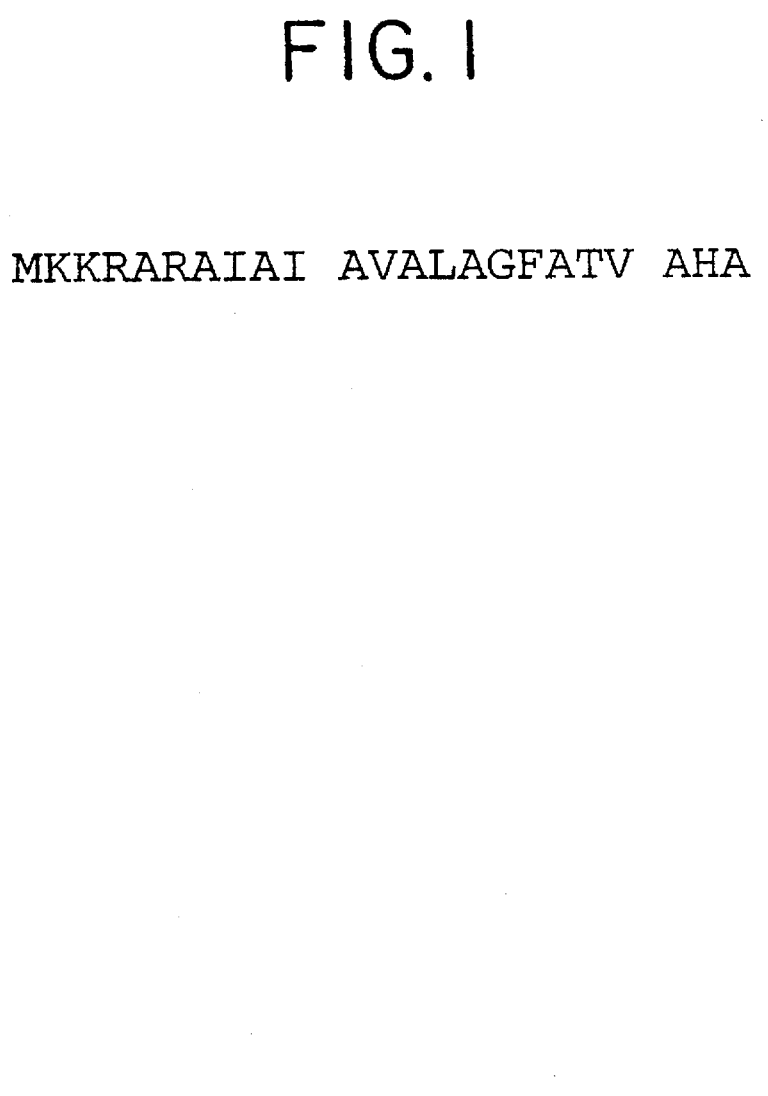

FIG. 1 depicts the amino acid sequence of a synthetic signal peptide, RH, useful in enhancing the secretion of certain polypeptides from *E. coli* cells (SEQ ID NO:1).

FIG. 2 depicts a degenerate nucleotide sequence encoding the signal peptide RH. "R" represents A or G; "W" represents A or T/U; "Y" represents C or T/U; and "D" represents A, G, or T/U (SEQ ID NO:2). The sequence was designed for preferential codon usage in prokaryotic cells.

FIG. 3 depicts one nucleotide sequence, RH11, which encodes the signal peptide RH (SEQ ID NO:3).

FIGS. 4A and 4B depict synthetic DNA sequences encoding a human BDNF amino acid sequence that is useful for preparation and expression of BDNF in a prokaryotic host cell. 4A (SEQ ID NO:4) depicts the sequence with a Met start codon, and 4B (SEQ ID NO:22) depicts the same sequence less the ATG Met start codon.

FIGS. 5A and 5B depict synthetic DNA sequences encoding a human NT-3 amino acid sequence that is useful for preparation and expression of NT-3 in a prokaryotic host cell. 5A (SEQ ID NO:5) depicts the sequence with a Met start codon, and 5B (SEQ ID NO:23) depicts the sequence less the ATG Met start codon.

DETAILED DESCRIPTION OF THE INVENTION

Figure 6:
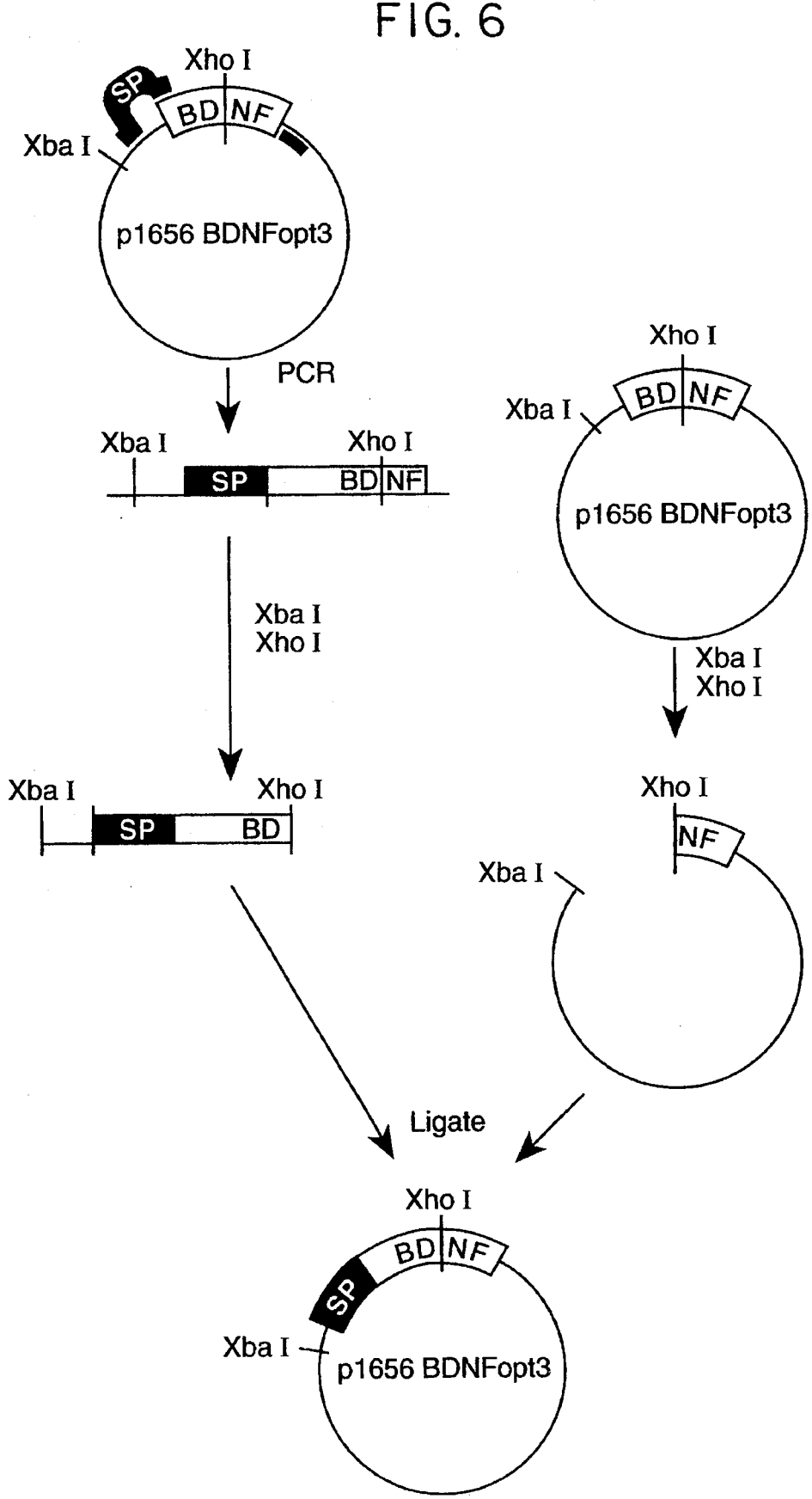
FIG. 6 is a schematic diagram of the strategy used to prepare a synthetic BDNF nucleic acid sequence linked at its 5' end to a nucleic acid sequence encoding the signal peptide RH. "SP" indicates the signal peptide sequence; selected restriction enzymes are shown. The relative size of each nucleic acid sequence is not to scale.

This invention is based on the unexpected discovery that certain synthetic signal peptide sequences serve to enhance the amount of NGF polypeptides secreted from some prokaryotic host cells.

Preparation of the Invention

The present invention contemplates the use of the signal peptide RH to enhance expression and secretion of polypeptides of the nerve growth factor (NGF) family synthesized and expressed in prokaryotic host cells. These polypeptides are referred to herein as "NGF polypeptides".

In addition, the invention provides a means to produce an NGF polypeptide lacking a methionine at its amino terminus. Such NGF polypeptides are referred to herein as "Met-less" NGF polypeptides.

1. Preparation of RH Nucleic Acid Sequences

Included within the scope of this invention are all possible nucleic acid sequences encoding the signal peptide RH. The partially degenerate codon nucleic acids (i.e., designed for preferential codon usage in prokaryotic cells) for RH are set forth in FIG. 2. One of the preferred nucleic acids encoding RH is RH11, the sequence of which is set forth in FIG. 3.

The nucleic acids encoding RH can readily be prepared using methods well known in the art, such as those set forth by Engels et al. (*Angew. Chem. Intl. Ed.*, 28:716–734 [1989]). A preferred method for synthesis is polymer-supported synthesis using standard phosphoramidite chemistry.

2. Preparation of DNA encoding NGF Polypeptides

Included within this invention is a method to prepare a NGF polypeptide from any mammalian source, including without limitation, human, bovine, and porcine. A preferred source is human. The NGF polypeptides include in the scope of this invention are, without limitation, BDNF (brain-derived neurotrophic factor), NT-3 (neurotrophin-3, also referred to as NGF-3), NGF (nerve growth factor), NT-4 (neurotrophin-4), NT-5 (neurotrophin-5), and other members of this family related by significant amino acid or nucleic acid sequence homology such as that exhibited by the presently known members of this family.

A DNA sequence encoding the NGF polypeptides contemplated herein may be isolated and obtained in suitable quantity using one or more methods that are well known in the art. These methods and others useful for isolating such DNA are set forth, for example, in Sambrook et al. (*Molecular Cloning: A Laboratory Manual*, Cold Spring Harbor Laboratory Press, Cold Spring Harbor, N.Y. [1989]) and in Berger and Kimmel (*Methods in Enzymology: Guide to Molecular Cloning Techniques*, vol. 152, Academic Press, Inc., San Diego, Calif. [1987]).

Preferred nucleic acid sequences for BDNF are those set forth in FIGS. 4A and 4B. Preferred nucleic acid sequences for NT-3 are those set forth in FIGS. 5A and 5B.

Where the amino acid sequence of the NGF polypeptide is known, a probable and functional nucleic acid encoding the polypeptide may be inferred using known and/or preferred codons for each amino acid residue.

Where the nucleic acid sequence of the NGF polypeptide is completely known, this sequence may be synthesized, in whole or in part, using chemical synthesis methods such as those described in Engels et al. (*Angew. Chem. Int. Ed. Engl.*, 28:716–734 [1989]). These methods include, inter alia, the phosphotriester, phosphoramidite and H-phosphonate methods of nucleic acid synthesis. Typically, the DNA encoding the polypeptide will be several hundred base pairs (bp) or nucleotides in length. Nucleic acids larger than about 100 nucleotides in length can be synthesized as several fragments, each fragment being up to about 100 nucleotides in length. The fragments can then be ligated together, as described below, to form a full length nucleic acid encoding the NGF polypeptide.

Alternatively, the nucleic acid encoding the NGF polypeptide may be obtained by screening an appropriate cDNA (i.e., prepared from a tissue source believed to express the polypeptide) or genomic library using one or more nucleic acid probes (oligonucleotides, cDNA or genomic DNA fragments with an acceptable level of homology to the nucleic acid to be cloned, and the like) that will hybridize selectively with the desired nucleic acid.

Another suitable method for obtaining a nucleic acid encoding the NGF polypeptide is the polymerase chain reaction (PCR). However, successful use of this method requires that enough information about the nucleic acid sequence encoding the NGF polypeptide is available so as to design suitable oligonucleotide primers useful for amplification of the nucleic acid sequence.

Where the method of choice for preparing the nucleic acid encoding the NGF polypeptide requires the use of oligonucleotide primers or probes (e.g. PCR, cDNA or genomic library screening), the oligonucleotide sequences selected as probes or primers should be of adequate length and sufficiently unambiguous so as to minimize the amount of non-specific binding that will occur during library screening or PCR. The actual sequence of the probes or primers is usually based on conserved or highly homologous sequences or regions from the same or a similar gene from another organism. Optionally, the probes or primers can be degenerate.

In cases where only the amino acid sequence of the NGF polypeptide is known, a probable and functional nucleic acid encoding the polypeptide sequence may be inferred using known and preferred codons for each amino acid residue. This sequence can then be chemically synthesized using methods described above.

This invention includes preparation of NGF polypeptide mutant sequences. A mutant sequence as used herein contains one or more nucleotide substitutions, deletions, and/or insertions as compared to the wild type sequence. The nucleotide substitution, deletion, and/or insertion can give rise to a NGF polypeptide that is different in its amino acid sequence from the wild type amino acid sequence. Preparation of such mutants is well known in the art, and is described for example in Wells et al. (*Gene*, 34:315 [1985]), and in Sambrook et al, supra.

3. Preparation of NGF Polypeptide Precursor

A nucleic acid encoding the NGF polypeptide precursor (i.e., the form containing the signal peptide sequence) may be prepared using any one of a variety of methods. In one method, a nucleic acid encoding RH may be directly ligated to the nucleic acid encoding the NGF polypeptide, provided that the nucleic acid encoding the NGF polypeptide does not contain the codon for the amino terminal methionine. Ligation of the two nucleic acids can be accomplished by blunt ligation or by designing a suitable restriction endonuclease site into the 3' end of the RH nucleic acid, using ligase enzyme and following the manufacturer's protocol, or by methods well known in the art such as those set forth by Sambrook et al., supra.

Alternatively, the nucleic acid encoding RH can be connected to the NGF polypeptide nucleic acid sequence using PCR. Here, the RH nucleic acid containing the entire RH sequence, plus an additional 15–21 nucleotides at its 3' end that contains the first (i.e., 5') 5 to 7 codons of the nucleic acid sequence encoding a NGF polypeptide excluding the Met codon (usually ATG), is used as a first PCR primer.

The RH/5' NGF nucleic acid primer is synthesized using well known methods such as standard phosphoramidite chemistry. The second PCR primer can be a nucleic acid that is complimentary to the last 6–8 codons (18–24 nucleotides) of the NGF nucleic acid, i.e., the codons at the 3' end of this nucleic acid. In this manner, using PCR, a nucleic acid sequence can be generated that consists of RH linked to the full length nucleic acid encoding NGF polypeptide less the amino terminal Met codon of the nucleic acid encoding this NGF polypeptide.

One other method useful for preparing the nucleic acid encoding the NGF precursor polypeptide also uses PCR. Here, the full length nucleic acid encoding the NGF polypeptide (that may contain the amino terminal Met codon) is first inserted into a cloning or expression vector. PCR is then used to prepare a nucleic acid containing an RH sequence linked to the full length nucleic acid encoding the NGF polypeptide. The PCR primers are similar to those described above. One primer used for PCR is complimentary to the vector sequence located 3' to the region of the nucleic acid encoding the NGF polypeptide. The other primer contains in the order 5' to 3', a portion (about 12–25 nucleotides) of the vector sequence that is immediately 5' to the NGF-coding sequence; a full length nucleotide sequence encoding the RH signal peptide, and the nucleotide sequence encoding the first 5–8 amino acids excluding the amino terminal Met of the NGF polypeptide. When this primer is hybridized to the vector containing the nucleic acid insert encoding the NGF polypeptide, the vector sequence portion and the sequence portion encoding the NGF polypeptide can hybridize to the primer while the RH sequence portion cannot. The RH portion can form a loop structure.

The other PCR primer for use in this method can be a nucleic acid sequence that is complimentary to the last 6–8 codons (18–24 nucleotides) of the nucleic acid encoding NGF polypeptide, or to a portion of the vector sequence 3' to the NGF nucleic acid sequence.

During PCR, the amplified nucleic acid product will contain, 5' to 3', a portion of 5' vector sequence, a RH signal peptide sequence, the full length nucleic acid sequence encoding the NGF polypeptide, less the amino terminal Met codon, and a portion of 3' vector sequence. After PCR, the PCR product can be cut with suitable restriction enzymes to generate a nucleic acid encoding a precursor form of a NGF polypeptide, which yields an amino-terminal Met-less NGF polypeptide after the RH signal peptide is cleaved during secretion.

4. Preparation/Selection of a Vector

Any expression vector that is functional in the selected prokaryotic host cell may be used provided that the vector contains all of the necessary nucleic acid components or elements to ensure expression of the NGF precursor polypeptide.

Typically, the vector will contain a promoter, an origin of replication element, a transcriptional termination element, a ribosome binding site element, a polylinker region for inserting the nucleic acid encoding the polypeptide to be expressed, and a selectable marker element.

A. Promoter Element

The promoter may be homologous (i.e., from the same prokaryotic species and/or strain as the host cell), heterologous (i.e., from a source other than the prokaryotic host cell species or strain), or synthetic. As such, the source of the promoter may be any unicellular prokaryotic or eukaryotic organism, any vertebrate or invertebrate organism, or any plant, provided that the promoter is functional in and can be regulated by the host cell. The more preferred promoters of this invention are inducible promoters such as those of bacteriophage lambda origin, i.e., lambda promoters such as the $P_R$ or $P_L$ promoters, the $T_5$ promoter or the $T_7$ promoter; bacterial promoters such as lac, tac (a composite of the trp and lac promoters), trp, and tna. A most preferred promoter is the $P_L$ promoter.

The promoter nucleic acid sequences useful in this invention may be obtained by any of several methods well known in the art. Typically, promoters useful herein will have been previously identified by mapping and/or by restriction endonuclease digestion and can thus be isolated from the proper tissue source using the appropriate restriction endonucleases. In some cases, the promoter may have been sequenced. For those promoters whose DNA sequence is known, the promoter may be synthesized using the methods described above for nucleic acid synthesis or cloning.

Where all or only portions of the promoter sequence are known, the promoter may be obtained using PCR and/or by screening a genomic library with suitable oligonucleotide and/or promoter sequence fragments from the same or another species.

Where the promoter sequence is not known, a fragment of DNA containing the promoter may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

B. Origin of Replication Element

This component is typically a part of prokaryotic expression vectors purchased commercially, and aids in the amplification of the vector in a host cell. Amplification of the vector to a certain copy number can, in some cases, be important for optimal expression of the NGF polypeptide. If the vector of choice does not contain an origin of replication site, one may be chemically synthesized based on a known sequence, and ligated into the vector.

C. Transcription Termination Element

This element is typically located 3' to the end of the NGF polypeptide coding sequence and serves to terminate transcription of the NGF polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

D. Selectable Marker(s) Element

Selectable marker genes encode proteins necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

E. Ribosome Binding Site Element

This element, commonly called the Shine-Dalgarno sequence, is necessary for translation initiation of a mRNA. The element is typically located 3' to the promoter and 5' to the coding sequence of the polypeptide to be synthesized. The Shine-Dalgarno sequence is varied but is typically a polypurine (i.e., having a high A-G content). Many Shine-Delgarno sequences have been identified, each of which can be readily synthesized using methods set forth above.

All of the elements set forth above, as well as others useful in this invention, are well known to the skilled artisan and are described, for example, in Sambrook et al. (*Molecular Cloning:A Laboratory Manual*, Cold Spring Harbor Laboratory Press, Cold Spring Harbor, N.Y. [1989]) and Berger et al., eds. (*Guide to Molecular Cloning Techniques*, Academic Press, Inc., San Diego, Calif. [1987]).

F. Construction of Vectors

The vectors most useful in practicing this invention are any expression vector that is compatible with the prokaryotic host cell selected.

In certain cases, some of the various vector elements listed above may be already present in commercially available vectors such as pUC18, pUC19, the pGEM vectors (Promega Corp, Madison, Wis.), the pBluescript® vectors such as pBIISK+/− (Stratagene Corp., La Jolla, Calif.), and the like, all of which are suitable for prokaryotic host cells, and suitable for use to practice this invention.

Where one or more of the elements are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

Preferred vectors of this invention are pCFM1656 (deposited on Feb. 24, 1993 under the Budapest Treaty with the American Type Culture Collection, 12301 Parklawn Drive, Rockville, Md. 20852, as accession number 69576), pGEM, the pBluescript® vectors, pUC18, and pUC19. Plasmid pCFM1656 requires a culturing temperature from about 30° C. to about 42° C. to obtain an increase in the plasmid copy number; increasing the temperature above about 42° C. inactivates the CI857 repressor element of the PL promoter.

The final vector used to practice this invention is typically constructed from a starting vector such as a commercially available vector. This vector may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

After the vector has been constructed and the NGF nucleic acid has been inserted into the proper site of the vector, the completed vector may be inserted into a prokaryotic host cell for amplification and NGF polypeptide expression. The prokaryotic cells typically used are any strain of *E. coli* that is compatible with the promoter on the vector such that the promoter is functional in the *E. coli* cell. Preferably, the selected strain will provide the regulatory elements that control the promoter such that expression of the NGF polypeptide is properly induced. Such strains as *E. coli* strains FM-5 (deposited on May 19, 1989 under the Budapest Treaty with the ATCC as accession number 53911), DH5-α, JM-101, and the like are suitable. In addition, other gram-negative bacteria such as *salmonella*, as well as gram-positive bacteria such as *bacillus* and other prokaryotes may also be suitable as host cells.

Insertion (also referred to as "transformation" or "transfection") of the vector into the selected host cell may be accomplished using such methods as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

The host cells containing the vector (i.e., transformed) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

5. Evaluation of Secretion

The amount of NGF polypeptide secreted from the host cell and thereby converted to the mature, Met-less form can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays.

To conduct some of the assays listed above, it may be necessary to first manipulate the host cell culture material in order to extract the polypeptide. Typically, the amount of processed, or mature, polypeptide secreted by the host cell will be compared to the total amount of polypeptide expressed (mature plus precursor polypeptide). Extracts of host cells can be prepared using standard methods in the art such as those set forth by Cull et al. (*Meth. Enz.,* 182:147–153 [1990]). If the host cells used are gram-positive bacteria or other prokaryotes that possess only a single cytoplasmic membrane, the secreted polypeptide can be found in the cell culture medium. Where the host cells are gram-negative bacteria such as *E. coli,* or other prokaryotes with two membranes (inner and outer membranes), the majority of the secreted polypeptide can be found in the periplasmic space, i.e., the space between the inner and outer membranes.

Collection of the unprocessed form of the NGF polypeptide (i.e., the precursor form) will typically require extracting the polypeptide from the host cell. For most analyses such as gel-electrophoresis, Western blotting and dot-blots, the NGF precursor polypeptide need not be purified. Rather, the host cells containing it can simply be collected by pelleting in a centrifuge, and then lysed using standard methods. Cellular debris (membranes, cell wall material and the like) can be separated by pelleting in a centrifuge, and the soluble fraction can then be loaded directly on to a gel or a dot-blot for further analysis.

The methods used to collect the processed, or secreted form of the NGF polypeptide will depend on whether the polypeptide is located in the periplasm (gram-negative bacteria) or in the culture medium (gram-positive bacteria and other prokaryotes).

If it is anticipated that the NGF polypeptide will be found in the culture medium, an aliquot of the culture medium may be directly used for gel electrophoresis, dot-blot analysis, and/or immuno-precipitation.

If it is expected that the NGF polypeptide will be found primarily in the periplasmic space, the contents of the periplasm, including inclusion bodies if the processed polypeptide has formed such complexes, can be extracted from the host cell using any standard technique known to the skilled artisan. For example, the host cells can be lysed to release the contents of the periplasm by French press, homogenization, and/or sonication. The homogenate can then be centrifuged.

If the NGF polypeptide has formed inclusion bodies in the periplasm, the inclusion bodies can often bind to the inner and/or outer cellular membranes and thus will be found primarily in the pellet material after centrifugation. The pellet material can then be treated with a chaotropic agent such as guanidine or urea to release, break apart, and solubilize the inclusion bodies. The NGF polypeptide in its now soluble form can then be analyzed using gel electrophoresis, immunoprecipitation or the like. If it is desired to isolate the NGF polypeptide, isolation may be accomplished using standard methods such as those set forth below and in Marston et al. (*Meth. Enz.,* 182:264–275 [1990]).

If NGF polypeptide inclusion bodies are not formed to a significant degree in the periplasm of the host cell, the NGF polypeptide will be found primarily in the supernatant after centrifugation of the cell homogenate, and the NGF polypeptide can be isolated from the supernatant using methods such as those set forth below.

In those situations where it is preferable to partially or completely isolate the precursor and/or the mature form(s) of the NGF polypeptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography.

In some cases, it may be preferable to use more than one of these methods for complete purification.

The invention may be more readily understood by reference to the following examples. These examples should not be construed in any way as limiting the scope of the invention.

EXAMPLES

Example 1

DDNF Secretion

A. Preparation of DNA Constructs

Human brain derived neurotrophic factor (BDNF) was prepared for expression in *E. coli* cells as follows. First, a synthetic BDNF gene was designed to provide for improved expression in *E. coli* cells. This gene had several codons altered at one or more bases as compared to the naturally occurring human BDNF nucleic acid sequence. The sequence of the synthetic gene, called BDNFopt3, is set forth in FIG. 4. The gene encodes a methionine (ATG) at the 5' end of the gene.

BDNFopt3 was prepared with polymer-supported synthesis using standard phosphoramidite chemistry methods. Due to the length of BDNFopt3, the gene was synthesized as four separate segments: segment 1 is 104 bases and contains some 5' untranslated sequence corresponding to vector sequence, an XbaI restriction site, an ATG start codon, and the first 76 bases of the BDNFopt3 nucleic acid sequence; segment 2 contains the next 117 bases of BDNFopt3; segment 3 contains the next 107 bases of BDNFopt3; and segment 4 contains the remaining 57 bases of BDNFopt3 along with the TAA stop codon, a BamHI restriction site sequence, and 5 additional nucleotides. The segments were ligated together using standard ligation protocols. Prior to ligation, three oligonucleotides were hybridized to the BDNFopt3 gene fragments to ensure that the four gene segments would be ligated together in the proper order. Each of the three oligonucleotides used spans one of the BDNFopt3 gene fragment junctions. The nucleic acid sequence of each of these oligonucleotides is set forth below:

ACTGCGGTTTTCTTATCAGC          (SEQ ID NO: 6)

CAGCCTTCTTTAGTGTAACC          (SEQ ID NO: 7)

GGATGAAGCGCCAGCCGATA          (SEQ ID NO: 8)

After ligation of the segments, a small portion of the ligation mixture with the full length single-stranded BDNFopt3 gene was used as a template for PCR in order to amplify this gene. The primers used for PCR amplification were:

TTGATTCTAGAAGGAGGAA           (SEQ ID NO: 9)

TCCGCGGATCCTTAGCGGCC          (SEQ ID NO: 10)

Twenty-five cycles of PCR were conducted using the following conditions: denaturing was at 94° C. for one minute; annealing was at 55° C. for one minute; and extension was at 72° C. for two minutes. The amplified fragment was purified from an agarose gel using the GENECLEAN II kit (Bio 101, Inc., La Jolla, Calif.), and digested with the restriction enzymes XbaI and BamHI. The fragment was then inserted into the vector pCFM1656 (ATCC accession number 69576) previously cut with XbaI and BamHI. This vector containing the full length BDNFopt3 gene, called pCFM1656/BDNFopt3, was used as a template to prepare the secretable form of the BDNFopt3 gene (i.e., containing a signal sequence). The cloning strategy used to prepare a secretable form of BDNFopt3 is depicted in FIG. 6.

Degenerate oligonucleotide sequences encoding the signal peptide sequence set forth in FIG. 2 were prepared using polymer-supported synthesis and standard phosphoramidite chemistry. Each sequence contained at its 5' end about 24 bases of pCFM1656 vector sequence located 5' to the BDNFopt3 gene sequence in pCFM1656/BDNFopt3 and at its 3' end about 18 bases encoding the first 6 amino acids of BDNFopt3 (excluding the amino terminal methionine, which was omitted in order to prepare a Met-less form of secreted BDNFopt3).

To prepare the secreted form of BDNFopt3, oligonucleotides with the degenerate RH signal peptide codons, and a second oligonucleotide that is complimentary to the vector sequence downstream from the 3' end of the BDNFopt3 gene (shown below as SEQ ID NO:11), were annealed to pCFM1656/BDNFopt3.

GTTGCTGCGATTCTCACCAA          (SEQ ID NO: 11)

The polymerase chain reaction (PCR) was then used to synthesize a gene encoding the entire BDNFopt3 sequence attached at its 5' end to a nucleic acid encoding the RH signal peptide sequence. PCR was conducted using reagents and taq DNA polymerase obtained from Boehringer Mannheim Biochemicals, Inc. Twenty-five cycles of PCR were conducted as follows: denaturation was at 94° C. for 1 minute; annealing was at 50° C. for 1 minute, and extension was at 72° C. for 2 minutes. After PCR, the PCR product (about 574 base pairs encoding BDNFopt3 plus the RH signal peptide) were run on a 0.8% agarose gel, and the 574 base pair fragment was cut out of the gel and purified using the GENECLEAN II kit (Bio 101, Inc.) and following the manufacturer's instructions. The purified fragment was digested with XbaI and XhoI to generate a DNA fragment of about 200 base pairs encoding the signal peptide RH and approximately the 5' one-third of the BDNFopt3 gene. The vector pCFM1656/BDNFopt3 was digested with XbaI and XhoI, the small fragment encoding the 5' end of BDNFopt3 was removed, and the 200 base pair RH/BDNFopt3sequence was ligated into this cut vector. Ligation was overnight at about 16° C. using ligase buffer and enzyme obtained from Boehringer Mannheim, Inc., and carrying out the reaction according to the manufacturer's instructions.

After ligation, the plasmids were inserted (transformed) into competent *E. coli* K-12 cells of strain FM-5 (ATCC accession number 53911). Insertion of the plasmid was accomplished using the standard calcium chloride procedure as set forth in Sambrook et al., supra. The transformed cells were cultured overnight at about 30° C. on standard Luria broth ("LB") agar plates containing kanamycin at about 50 μg/ml. After culturing, 16 individual colonies were selected, inoculated into LB containing kanamycin at about 50 μg/ml, and cultured overnight at about 30° C. on a shaker. After culturing, the cells were diluted about 1:10 into standard Terrific broth ("TB"; Sambrook et al., supra) containing kanamycin, and allowed to grow at about 30° C. to a density of about 0.5–0.8 OD600 at which time the temperature was increased to about 42° C. to induce expression and secretion of BDNFopt3. After about 4 hours, approximately 1 mg of wet cell mass was pelleted and then lysed by boiling for about 10 minutes in about 100 μl of standard Tris-glycine SDS-PAGE denaturing/reducing buffer (62.5 mM Tris-HCl, pH6.8, 2% SDS, 0.0025% Bromophenol blue, 10% glycerol, 2.5% β-mercapto-ethanol). About 10 μl of this mixture was then run on a standard SDS polyacrylamide gel (about 18 percent acrylamide). The gel was run at a constant voltage of about 130 volts for about 2.5 hours. The gels, sample buffer and running buffer were all purchased from NOVEX, Inc. (San Diego, Calif.) and used according to the manufacturer's instructions.

As a control system, a nucleic acid encoding the signal peptide for OmpA was attached to the BDNFopt3 gene using the same procedures as set forth above for preparation of the RH/BDNFopt3 nucleic acid. The oligonucleotide sequence used to generate the OmpA signal peptide was:

ATTCTAGAAGGAGGAATAACATATGAAAAAGACAGCTATCGCGATT
GCAGTGGCACTGGCTGGTTTCGCTACCGTAGCGCAGGCCCACTCTG
ACCCGGCTCGT.

As for the RH oligonucleotides, the OmpA oligonucleotide contained at its 5' end about 24 bases of the pCFM1656 vector sequence, and at its 3' end about 18 bases encoding the first 6 amino acids of BDNFopt3 (excluding the amino terminal Met).

B. Analysis of Signal Peptide Nucleic Acid Sequences

The efficiency of the various nucleotide sequences encoding the signal peptide RH was analyzed as the percentage of the amount of processed BDNFopt3 (signal peptide clipped off of the BDNFopt3 polypeptide) as compared to the total BDNFopt3 protein produced (processed plus unprocessed). To compare the two forms of BDNFopt3, the SDS-gel was stained with Commassie blue, and scanned after staining to determine the relative amount of each form. The molecular weight of the unprocessed BDNFopt3 precursor polypeptide is about 15.8 kD, while the molecular weight of the processed form of BDNFopt3 is about 13.5 kD. Thus, the two forms of BDNFopt3 show distinctly different bands on an SDS-denaturing polyacrylamide gel.

For a number of the RH/BDNFopt3 polypeptides, both of the bands (i.e., processed and unprocessed BDNFopt3) were visually apparent by both staining the gel with Coomasssie blue dye and by Western blotting the gel and detecting BDNFopt3 on the Western blot with a polyclonal anti-BDNF antibody. One RH nucleic acid sequence, RH11, appeared by visual inspection to have processed more BDNFopt3 as compared with the other RH nucleic acid sequences such as RH12, and with the OmpA nucleic acid sequence. The gel was scanned using an Ultrascan XL (Pharmacia LKB) to determine the relative amounts of processed and unprocessed BDNF for the different RH signal peptide nucleic acid sequences and the OmpA signal peptide nucleic acid sequence. The results of the scan for RH11, RH12, and OmpA nucleic acid sequences are shown in Table 1 below. The results are reported as area under the curve (Absorbance x width in millimeters of the protein band on the gel) obtained from scanning the gel.

TABLE 1

|  | OmpA | RH11 | RH12 |
| --- | --- | --- | --- |
| Unprocessed | 0.64 | 0.07 | 1.61 |
| Processed | 0.34 | 0.65 | 0.73 |
| Percent Processed | 34.7 | 90.3 | 31.2 |

As is apparent, the use of the RH11 signal peptide nucleic acid sequence resulted in more effective processing of BDNFopt3 as compared to the use of the OmpA or RH12 sequences.

Example 2

NT-3 Secretion

A. Preparation of DNA Constructs

A synthetic gene encoding human NT-3 was prepared for expression in *E. coli* cells. The gene was designed to improve expression in these cells by using preferred bacte- (SEQ ID NO: 12)

rial codons. The sequence of this synthetic gene is set forth in FIG. 5.

The synthetic gene, called NT-3opt3, was prepared by polymer supported synthesis using standard phosphoramidite chemistry methods. Due to the length of NT-3opt3, it was prepared as four separate nucleic acid fragments ranging in length from 94 to 104 nucleotides. The fragment encoding the 5' portion of the NT-3opt3 gene contained some non-coding sequence 5' to the ATG start codon to provide an XbaI site. The fragment encoding the 3' portion of the NT-3opt3 gene contained some non-coding sequence at the 3' end which provides a BamHI restriction site.

After synthesis, the fragments were ligated together using oligonucleotide junction nucleic acids whose sequences are complimentary to the regions around each ligation junction. Annealing and ligation were accomplished using standard protocols. The oligonucleotide sequences used as junction sequences are set forth below:

| | |
| --- | --- |
| AGCGGAGGATTTGTCGGTAA | (SEQ ID NO: 13) |
| CTTTGCAACGGGTTTCGTAG | (SEQ ID NO: 14) |
| GTTTTCGGAGGTCAGAGCAC | (SEQ ID NO: 15) |

A small fraction of the ligated mix with full length single-stranded NT-3opt3 gene was used as a template for PCR in order to amplify the NT-3opt3 gene. The following two oligonucleotides were used as primers for this PCR:

| | |
| --- | --- |
| TTGATTCTAGAAGGAGGAAT | (SEQ ID NO: 16) |
| TCCGCGGATCCTTAGGTACG | (SEQ ID NO: 17) |

Twenty-five cycles of PCR were conducted as follows: denaturing was at 94° C. for 1 minute; annealing was at 55° C. for 1 minute; and extension was at 72° C. for 2 minutes. The amplified fragment was purified from an agarose gel using the GENECLEAN II kit (Bio 101), digested with XbaI and BamHI, and inserted into the vector pCFM1656 previously cut with XbaI and BamHI. This plasmid containing the NT-3opt3 gene was used to prepare the NT-3opt3 gene containing a nucleic acid encoding the RH signal peptide sequence. The strategy used was comparable to that set forth for BDNFopt3 in Example 1 and depicted in FIG. 6.

Partially degenerate oligonucleotide sequences encoding the RH signal peptide sequence as set forth in FIG. 2 were synthesized using standard phosphoramidite DNA synthesis methods. Each sequence contained at its 5' end about 24 bases of the pCFM1656 vector sequence. Each sequence contained at its 3' end 18 bases encoding the first 6 amino acids of NT-3opt3 (excluding the first methionine amino acid residue, which was omitted in order to prepare an amino terminal Met-less form of secreted NT-3opt3).

To prepare a secreted form of NT-3opt3, the oligonucleotide sequences containing degenerate RH signal peptide codons were annealed to the pCFM1656/NT-3opt3 vector for PCR. A second oligonucleotide sequence that is complimentary to the 3' end of the vector sequence downstream from the NT-3opt3 gene was simultaneously annealed to pCFM1656/NT-3opt3. The polymerase chain reaction (PCR) was then used to synthesize a gene encoding the entire NT-3opt3 sequence attached at its 5' end to a nucleic acid encoding the RH signal peptide sequence.

PCR was conducted using reagents and taq DNA polymerase obtained from Boehringer Mannheim Biochemicals, Inc. Twenty-five cycles of PCR were conducted as follows: denaturation was at 94° C. for 1 minute; annealing was at 50° C. for 1 minute, and extension was at 72° C. for 2 minutes. After PCR, the PCR product (about 574 base pairs encoding NT-3opt3 and the signal peptide RH) were run on a 0.8% agarose gel, and the approximately 574 RH/NT-3opt3 nucleotide fragment was cut out of the gel and purified using the GENECLEAN II kit (Bio 101, Inc.) following the manufacturer's instructions. The purified fragment was digested with XbaI and HindIII to generate a DNA fragment of about 371 bp encoding the RH signal peptide and the 5' portion of the NT-3 gene. The vector pCFM1656/NT-3opt3 was digested with XbaI and HindIII, the fragment encoding the 5' portion of NT-3opt3 was removed and replaced by ligation with the approximately 371 base pair RH/NT3opt3 DNA sequence (produced by PCR). Ligation was overnight at 16° C. using ligase buffer and enzyme obtained from Boehringer Mannheim, Inc., and following the manufacturer's instructions.

B. Analysis of Signal Peptide Nucleic Acid Sequences

The efficiency of the various nucleotide sequences encoding the signal peptide RH was analyzed as the percentage of the amount of processed NT-3opt3 (signal peptide cleaved from the NT-3opt3 polypeptide) as compared to the total amount of NT-3opt3 expressed (processed plus unprocessed NT-3opt3). To compare the two forms of NT-3opt3, the SDS-gel was stained with Commassie blue, and scanned after staining to determine the relative amount of each form. The molecular weight of the unprocessed NT-3opt3 precursor polypeptide is about 15.9 kD, while the molecular weight of the processed form of NT-3opt3 is about 13.6 kD. Thus, the two forms of NT-3opt3 show distinctly different bands on an SDS-denaturing polyacrylamide gel.

For a number of the RH/NT-3opt3 polypeptides, the bands were visually apparent by both staining the gel with Coomasssie blue dye and by Western blotting the gel and detecting NT-3opt3 on the Western blot with a polyclonal anti-NT-3opt3 antibody. Two RH nucleic acid sequences, RH3, RH5, and RH11, appeared by visual inspection to have a higher percentage of processed NT-3opt3 as compared with other RH nucleic acid sequences. The sequences of RH3 (SEQ ID NO:18), RH4 (SEQ ID NO:19), RH5 (SEQ ID NO:20), and RH6 (SEQ ID NO:21) are set forth below; the sequence for RH11 is set forth in FIG. 3.

RH3:  (SEQ ID NO: 18)
ATGAAGAAACGTGCGCGCGCGATTGCAATTGCAGTAGCGCTGGCTG
GCTTTGCTACCGTAGCGCACGCG

RH4:  (SEQ ID NO: 19)
ATGAAAAAGCGCGCACGCGCTATCGCTATCGCTGTTGCTCTGGCTG
GCTTTGCAACTGTTGCTCATGCA

RH5:  (SEQ ID NO: 20)
ATGAAAAAGCGCGCACGCGCAATTGCGATTGCGGTTGCTCTGGCGG
GTTTCGCTACCGTTGCGCATGCG

RH6:  (SEQ ID NO: 21)
ATGAAAAAGCGCGCTCGTGCGATCGCGATTGCTGTAGCGCTGGCGG
GTTTTGCAACTGTAGCTCACGCG

After ligation, the plasmids were inserted (transformed) into competent E. coli K-12 cells strain FM-5 (A.T.C.C. accession number 53911). Insertion of the plasmid into E. coli cells was accomplished using the standard calcium chloride procedure as set forth in Sambrook et al., supra. The transformed cells were cultured overnight at about 30° C. on standard Luria broth ("LB") agar plates containing kanamycin at about 50 µg/ml. After culturing, 13 individual colonies were selected, inoculated into LB containing kanamycin at about 50 µg/ml, and cultured overnight at about 30° C. After culturing, the cells were diluted about 1:10 into standard Terrific broth ("TB"; Sambrook et al., supra) containing kanamycin, and allowed to grow at about 30° C. to a density of about 0.5–0.8 OD600 at which time the temperature was increased to about 42° C. to induce expression and secretion of NT-3opt3. After about 4 hours, approximately 1 mg of wet cell mass was pelleted and then lysed by boiling for about 10 minutes in about 100 µl of standard SDS-PAGE denaturing/reducing buffer (as described in Example I). About 10 µl of this mixture was then run on a standard SDS polyacrylamide gel (about 18 percent acrylamide). The gel was run at a constant voltage of about 130 volts for about 2.5 hours. The gels, sample buffer and running buffer were all purchased from NOVEX, Inc. (San Diego, Calif.) and used according to the manufacturer's instructions.

The gel was scanned as described in Example I to determine the relative amounts of processed and unprocessed NT-3opt3 for several different RH signal peptide nucleic acid sequences. The results of the scan for the activity of the nucleic acid sequences are shown in Table 2 below. The results are reported as area under the curve (Absorbance×width in millimeters of the protein band) obtained from scanning the gel.

TABLE 2

|  | RH3 | RH4 | RH5 | RH6 | RH11 |
|---|---|---|---|---|---|
| Unprocessed | 0.05 | 0.87 | 0.05 | 0.70 | 0.05 |
| Processed | 0.46 | 1.01 | 0.53 | 0.76 | 0.40 |
| Percent Processed | 90.2 | 53.7 | 91.4 | 52.1 | 88.9 |

All literature cited herein is specifically incorporated by reference.

We claim:

1. The peptide MKKRARAIAIAVALAGFATVAHA (SEQ ID NO:1) linked at its carboxyl terminus to the polypeptide BDNF.

2. The peptide MKKRARAIAIAVALAGFATVAHA (SEQ ID NO:1) linked at its carboxyl terminus to the polypeptide NT-3.

3. The peptide MKKRARAIAIAVALAGFATVAHA (SEQ ID NO:1) linked at its carboxyl terminus to the polypeptide NGF.

4. The peptide MKKRARAIAIAVALAGFATVAHA (SEQ ID NO:1) linked at its carboxyl terminus to the polypeptide NT-4.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Met Lys Lys Arg Ala Arg Ala Ile Ala Ile Ala Val Ala Leu Ala Gly
 1               5                  10                  15
    Phe Ala Thr Val Ala His Ala
                 20
```

( 2 ) INFORMATION FOR SEQ ID NO:2:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
ATGAARAARC  GYGCDCGYGC  DATYGCDATY  GCDGTWGCDC  TGGCDGGYTT  YGCDACYGTW      60
GCDCAYGCD                                                                   69
```

( 2 ) INFORMATION FOR SEQ ID NO:3:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
ATGAAAAAGC  GCGCGCGTGC  GATCGCGATC  GCGGTTGCGC  TGGCTGGCTT  CGCTACCGTT      60
GCGCACGCT                                                                   69
```

( 2 ) INFORMATION FOR SEQ ID NO:4:

( i ) SEQUENCE CHARACTERISTICS:
        ( A ) LENGTH: 363 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
ATGCACTCTG  ACCCGGCTCG  TCGTGGTGAA  CTGTCTGTTT  GTGATTCTAT  CTCTGAATGG      60
GTTACCGCGG  CTGATAAGAA  AACCGCAGTC  GACATGTCTG  GTGGCACTGT  TACCGTCCTC     120
GAGAAAGTTC  CTGTATCTAA  AGGTCAGCTG  AAACAATATT  CTACGAAAC   CAAATGCAAT     180
CCGATGGGTT  ACACTAAAGA  AGGCTGCCGT  GGCATCGACA  AACGTCATTG  GAACTCTCAG     240
```

| | | | | | |
|---|---|---|---|---|---|
| TGTCGTACTA | CCCAGTCTTA | TGTTCGTGCG | CTGACCATGG | ACTCCAAGAA | ACGTATCGGC | 300
| TGGCGCTTCA | TCCGTATTGA | CACTAGTTGC | GTTTGTACTC | TGACTATCAA | ACGTGGCCGC | 360
| TAA | | | | | | 363

( 2 ) INFORMATION FOR SEQ ID NO:5:

( i ) SEQUENCE CHARACTERISTICS:
        ( A ) LENGTH: 363 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

| | | | | | |
|---|---|---|---|---|---|
| ATGTACGCTG | AACACAAATC | CCACCGTGGT | GAATATTCCG | TTTGCGACTC | CGAATCCCTG | 60
| TGGGTTACCG | ACAAATCCTC | CGCTATCGAT | ATCCGTGGTC | ACCAGGTTAC | CGTTCTGGGT | 120
| GAAATCAAAA | CCGGTAACTC | CCCAGTAAAA | CAGTACTTCT | ACGAAACCCG | TTGCAAAGAA | 180
| GCTCGTCCGG | TTAAAAACGG | TTGCCGCGGT | ATCGACGACA | AACATTGGAA | CTCTCAGTGC | 240
| AAAACTAGTC | AGACCTACGT | TCGTGCTCTG | ACCTCCGAAA | ACAACAAGCT | TGTTGGTTGG | 300
| CGTTGGATTC | GTATCGACAC | CAGCTGCGTT | TGCGCTCTGT | CCCGTAAAAT | CGGTCGTACC | 360
| TAA | | | | | | 363

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

ACTGCGGTTT    TCTTATCAGC    20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CAGCCTTCTT    TAGTGTAACC    20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

GGATGAAGCG    CCAGCCGATA    20

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

| | |
|---|---:|
| TTGATTCTAG AAGGAGGAA | 19 |

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

| | |
|---|---:|
| TCCGCGGATC CTTAGCGGCC | 20 |

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

| | |
|---|---:|
| GTTGCTGCGA TTCTCACCAA | 20 |

( 2 ) INFORMATION FOR SEQ ID NO:12:

( i ) SEQUENCE CHARACTERISTICS:
        ( A ) LENGTH: 103 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

| | | | | | |
|---|---|---|---|---|---:|
| ATTCTAGAAG | GAGGAATAAC | ATATGAAAAA | GACAGCTATC | GCGATTGCAG | TGGCACTGGC | 60 |
| TGGTTTCGCT | ACCGTAGCGC | AGGCCCACTC | TGACCCGGCT | CGT | | 103 |

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

| | |
|---|---:|
| AGCGGAGGAT TTGTCGGTAA | 20 |

( 2 ) INFORMATION FOR SEQ ID NO:14:

( i ) SEQUENCE CHARACTERISTICS:

(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:14:

CTTTGCAACG GGTTTCGTAG    20

(2) INFORMATION FOR SEQ ID NO:15:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:15:

GTTTTCGGAG GTCAGAGCAC    20

(2) INFORMATION FOR SEQ ID NO:16:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:16:

TTGATTCTAG AAGGAGGAAT    20

(2) INFORMATION FOR SEQ ID NO:17:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:17:

TCCGCGGATC CTTAGGTACG    20

(2) INFORMATION FOR SEQ ID NO:18:

(i) SEQUENCE CHARACTERISTICS:
(A) LENGTH: 69 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:18:

ATGAAGAAAC GTGCGCGCGC GATTGCAATT GCAGTAGCGC TGGCTGGCTT TGCTACCGTA    60

GCGCACGCG    69

(2) INFORMATION FOR SEQ ID NO:19:

(i) SEQUENCE CHARACTERISTICS:
(A) LENGTH: 69 base pairs
(B) TYPE: nucleic acid
(C) STRANDEDNESS: single (D) TOPOLOGY: linear (i i) MOLECULE TYPE: cDNA (x i) SEQUENCE DESCRIPTION: SEQ ID NO:19:

| ATGAAAAAGC | GCGCACGCGC | TATCGCTATC | GCTGTTGCTC | TGGCTGGCTT | TGCAACTGTT | 60 |
|---|---|---|---|---|---|---|
| GCTCATGCA | | | | | | 69 |

(2) INFORMATION FOR SEQ ID NO:20:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:20:

| ATGAAAAAGC | GCGCACGCGC | AATTGCGATT | GCGGTTGCTC | TGGCGGGTTT | CGCTACCGTT | 60 |
|---|---|---|---|---|---|---|
| GCGCATGCG | | | | | | 69 |

(2) INFORMATION FOR SEQ ID NO:21:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:21:

| ATGAAAAAGC | GCGCTCGTGC | GATCGCGATT | GCTGTAGCGC | TGGCGGGTTT | TGCAACTGTA | 60 |
|---|---|---|---|---|---|---|
| GCTCACGCG | | | | | | 69 |

(2) INFORMATION FOR SEQ ID NO:22:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:22:

| CACTCTGACC | CGGCTCGTCG | TGGTGAACTG | TCTGTTTGTG | ATTCTATCTC | TGAATGGGTT | 60 |
|---|---|---|---|---|---|---|
| ACCGCGGCTG | ATAAGAAAAC | CGCAGTCGAC | ATGTCTGGTG | GCACTGTTAC | CGTCCTCGAG | 120 |
| AAAGTTCCTG | TATCTAAAGG | TCAGCTGAAA | CAATATTTCT | ACGAAACCAA | ATGCAATCCG | 180 |
| ATGGGTTACA | CTAAAGAAGG | CTGCCGTGGC | ATCGACAAAC | GTCATTGGAA | CTCTCAGTGT | 240 |
| CGTACTACCC | AGTCTTATGT | TCGTGCGCTG | ACCATGGACT | CCAAGAAACG | TATCGGCTGG | 300 |
| CGCTTCATCC | GTATTGACAC | TAGTTGCGTT | TGTACTCTGA | CTATCAAACG | TGGCCGCTAA | 360 |

(2) INFORMATION FOR SEQ ID NO:23:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (i i) MOLECULE TYPE: cDNA (xi) SEQUENCE DESCRIPTION: SEQ ID NO:23:

```
TACGCTGAAC  ACAAATCCCA  CCGTGGTGAA  TATTCCGTTT  GCGACTCCGA  ATCCCTGTGG    60
GTTACCGACA  AATCCTCCGC  TATCGATATC  CGTGGTCACC  AGGTTACCGT  TCTGGGTGAA   120
ATCAAAACCG  GTAACTCCCC  AGTAAAACAG  TACTTCTACG  AAACCCGTTG  CAAAGAAGCT   180
CGTCCGGTTA  AAAACGGTTG  CCGCGGTATC  GACGACAAAC  ATTGGAACTC  TCAGTGCAAA   240
ACTAGTCAGA  CCTACGTTCG  TGCTCTGACC  TCCGAAAACA  ACAAGCTTGT  TGGTTGGCGT   300
TGGATTCGTA  TCGACACCAG  CTGCGTTTGC  GCTCTGTCCC  GTAAAATCGG  TCGTACCTAA   360
```